United States Patent [19]

Noiles

[11] 3,967,620

[45] July 6, 1976

[54] VOLUME LIMITING CHAMBER

[75] Inventor: Douglas G. Noiles, New Canaan, Conn.

[73] Assignee: United States Surgical Corporation, New York, N.Y.

[22] Filed: Sept. 10, 1974

[21] Appl. No.: 504,733

[52] U.S. Cl. .................. 128/214 C; 210/DIG. 23; 210/446
[51] Int. Cl.² ..................................... A61M 5/14
[58] Field of Search .............. 210/391, 446, 321 R, 210/DIG. 23; 137/395, 183; 128/214 R, 214 C, 214.2, 227

[56] References Cited
UNITED STATES PATENTS

| 2,854,992 | 10/1958 | Hewitt | 128/214 R X |
| 3,216,419 | 11/1965 | Scislowicz | 128/214 C |
| 3,650,093 | 3/1972 | Rosenberg | 55/159 |
| 3,677,242 | 7/1972 | Shaye | 128/214 C |
| 3,882,026 | 5/1975 | McPhee | 210/446 |

FOREIGN PATENTS OR APPLICATIONS

| 1,182,016 | 2/1970 | United Kingdom | 128/214 C |

*Primary Examiner*—Dalton L. Truluck
*Attorney, Agent, or Firm*—Fleit & Jacobson

[57] ABSTRACT

An intravenous set has a volume limiting chamber for precisely controlling the volume of parenteral solution administered to a patient and a flexible drip chamber for determining the parenteral solution flow rate. The volume limiting chamber has a membrane valve which when wet will pass parenteral solution but will not pass air at normal intravenous administration pressures. An air bypass is provided in the volume limiting chamber so that air can bypass the membrane valve and enter the volume limiting chamber from the drip chamber when the drip chamber is squeezed to prime the intravenous set.

36 Claims, 5 Drawing Figures

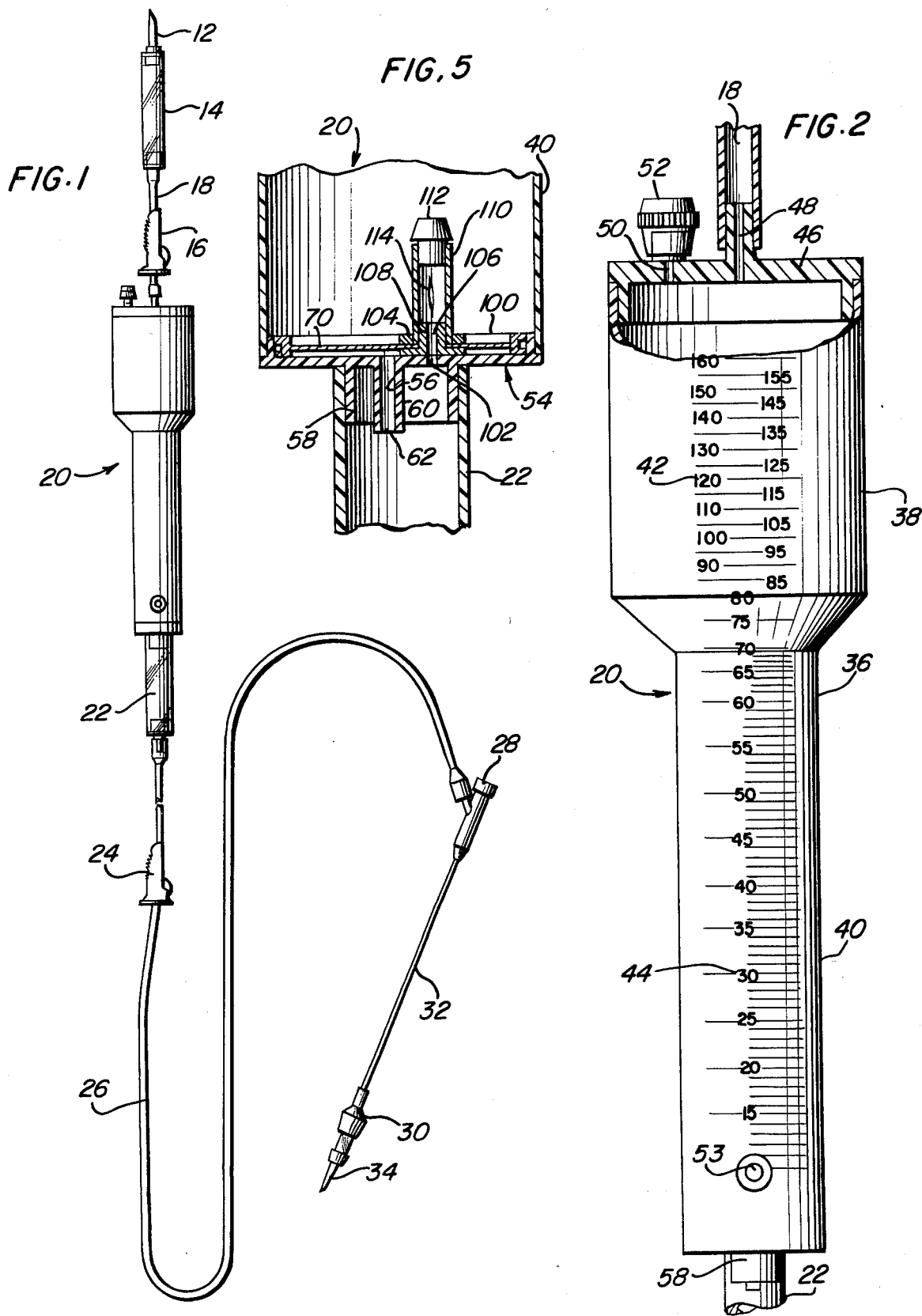

VOLUME LIMITING CHAMBER

BACKGROUND OF THE INVENTION

The present invention relates to an improved volume limiting chamber for use in the intravenous set.

Intravenous sets for the administration of parenteral solution to a patient typically include a piercer for insertion into a parenteral solution container, flexible tubing for transporting the parenteral solution from the container to the patient, a first or lower flow control clamp which acts on the flexible tubing to control the flow rate of the parenteral solution, and a needle adapter to which an intravenous needle is attached. The flow rate is determined by a flow meter such as a drip chamber positioned upstream of the lower clamp. The intravenous set may also include a volume limiting chamber positioned between the piercer and the drip chamber and a second or upper flow control clamp positioned upstream of the volume limiting chamber. The volume limiting chamber is used to precisely control the volume of parenteral solution administered to the patient.

The volume limiting chamber is normally designed to automatically shut off after a measured volume of parenteral solution is fed to the patient. This is accomplished in many intravenous sets by a membrane valve mounted in the bottom of the volume limiting chamber. Basically, the membrane valve comprises a material which when wet will pass parenteral fluid but will not pass air at normal intravenous administration pressures. In using an intravenous set of this type, both the upper and lower control clamps are closed and the piercer is inserted into the outlet of a parenteral solution container. The upper flow control clamp is then opened and the volume limiting chamber partially filled with parenteral solution. After the upper flow control clamp is again closed, the set must be primed. This is accomplished by opening the lower flow control clamp, squeezing the drip chamber and then closing the lower flow control clamp. The drip chamber is then released and will partially fill with parenteral solution. This priming step is repeated until the drip chamber is approximately one-half filled. The lower flow control clamp must be opened during the priming operation so that the membrane valve will not be damaged. This priming operation is tedious and time consuming and runs the risk of damaging the delicate membrane valve unless strictly followed.

Intravenous sets are also known in which the volume limiting chamber is automatically shut off by a float having a very thin, flexible diaphragm adapted to seat against a valve seat and close off the flow of liquid and air after a measured volume of solution is fed to the patient. Intravenous sets of this type can be primed without repeatedly opening and closing the lower flow control clamp. However, since the diaphragm only seats against the valve seat after the measured volume of solution is fed to the patient, the parenteral solution is not filtered during administration.

Accordingly, it is an object of the present invention to provide an improved volume limiting chamber.

It is another object of the present invention to provide an improved automatic shut off valve for use in an intravenous set.

It is a further object of the present invention to provide an improved volume limiting chamber having an automatic shut off valve.

It is still a further object of the present invention to provide an improved volume limitng chamber having an automatic shut off valve in which the intravenous set can be primed by squeezing and releasing the flexible drip chamber without simultaneously opening and closing the flow control clamps.

Yet another object of the present invention is to provide an improved volume limiting chamber having a membrane valve in which the membrane valve is mounted so that air can enter the volume limiting chamber from the drip chamber around the periphery of the membrane valve during priming.

Still another object of the present invention is to provide an improved volume limiting chamber having a membrane valve and a check valve for bypassing the membrane valve and allowing air to enter the volume limiting chamber from the drip chamber during priming.

A stll further object of the present invention is to provide an improved membrane filter for use in an intravenous set.

SUMMARY OF THE INVENTION

A volume limiting chamber is provided in accordance with the present invention for use in an intravenous set. The volume limiting chamber includes a membrane valve for automatically shutting off the intravenous set after a measured volume of parenteral solution is fed to the patient. A membrane valve will not pass air when wet under normal intravenous administration pressures and can easily be damaged if subjected to higher pressures. However, means are provided for bypassing the membrane valve and allowing air to enter the volume limiting chamber from the drip chamber when the membrane valve is wet. Accordingly, the intravenous set can be primed by squeezing and releasing the flexible drip chamber positioned downstream of the volume limiting chamber without simultaneously adjusting the flow control clamps and without danger of damaging the delicate membrane valve.

BRIEF DESCRIPTION OF THE DRAWINGS

FIG. 1 is a schematic view of an intravenous set having the volume limiting chamber of the present invention incorporated therein;

FIG. 2 is an enlarged view, partly in section, of the volume limiting chamber of the present invention;

FIG. 5 is a vertical cross-sectional view of the bottom of the volume limiting chamber of the present invention showing the membrane valve and a second embodiment of the air bypass.

DESCRIPTION OF THE PREFERRED EMBODIMENTS

Figure 3:
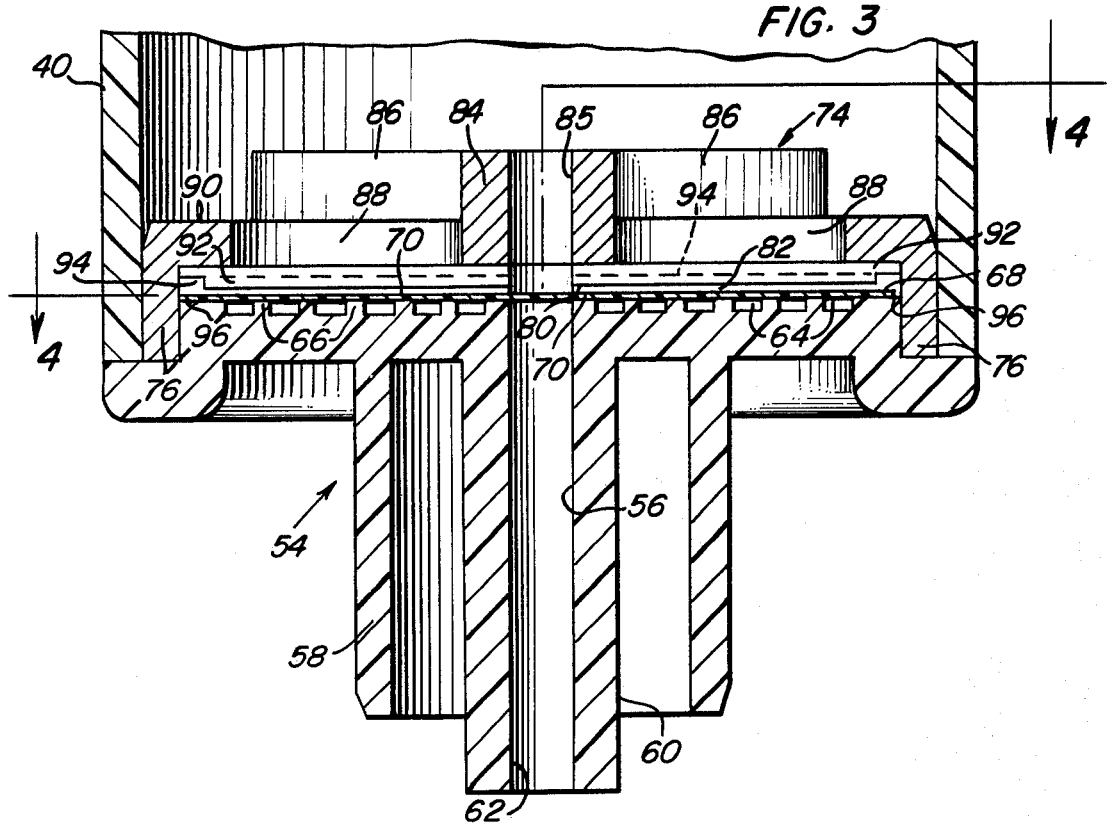
FIG. 3 is a vertical cross-sectional view of the bottom of the volume limiting chamber of the present invention showing the membrane valve and the air bypass.

Referring now to FIG. 1, the volume limiting chamber of the present invention is shown in an intravenous set for administering parenteral solution to a patient. The intravenous set includes piercer 12 for attaching the intravenous set to the outlet of a parenteral solution container. Drip chamber 14 is attached to piercer 12 and is used to determine the flow rate of parenteral solution issuing from the parenteral solution container.

This flow rate can be controlled by first or upper compression clamp 16 which acts on flexible plastic tubing 18. Tubing 18, typically formed from polyvinyl chloride, connects drip chamber 14 to volume limiting chamber 20 of the present invention. Flexible drip chamber 22 is connected to the bottom of volume limiting chamber 20 and is used to determine the flow rate of parenteral solution issuing from volume limiting chamber 20. This flow rate can be controlled by second or lower compression clamp 24 which acts on flexible plastic tubing 26. Tubing 26, also typically formed from polyvinyl chloride, connects drip chamber 22 to Y-injection site 28. Y-injection site 28 can be used for injecting additional medication into the parenteral fluid flow line downstream from volume limiting chamber 20. Y-injection site 28 is connected to injection bulb 30 by flexible plastic tubing 32 which is similar to tubings 18 and 26. Finally, the intravenous set includes needle adapter 34 for attachng an intravenous needle to the set.

Referring now to FIG. 2, volume limiting chamber 20, typically made from a styrene-acrylonitrile polymer, comprises side walls 36 having upper portion 38 and lower portion 40. Upper portion 38 is generally oval in cross-section and has a larger cross-sectional area than lower portion 40 which is generally circular in cross-section. Upper porton 38 has a first set of indicia 42 associated therewith and lower portion has a second set of indicia 44 associated therewith for determining the volume of parenteral fluid in the volume limiting chamber. Upper portion 38 of the volume limiting chamber is closed by upper end cap 46 which defines inlet conduit 48. Inlet conduit 48 is connected to flexible plastic tubing 18. Upper end cap 46 also defines air vent 50 having a semipermeable membrane (not shown) mounted therein. Air vent 50 is covered by removable cap 52. The semipermeable membrane is permeable to air but not to parenteral solution. The air vent is used to vent air which is displaced from volume limiting chamber 20 as parenteral solution is added to the chamber. Volume limiting chamber 20 also includes injection site 53 for injecting medication into the volume limitng chamber.

Figure 4:
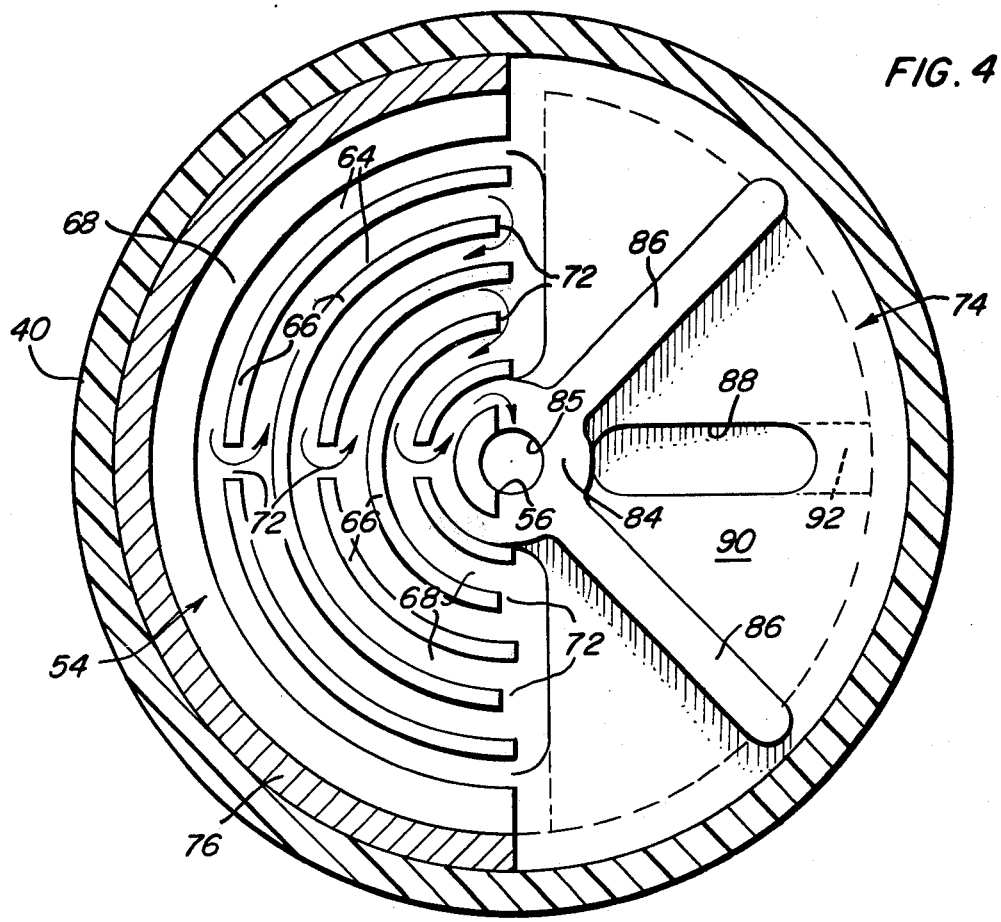
FIG. 4 is a horizontal cross-sectional view taken along line 4—4 of FIG. 3.

Referring now to FIGS. 3 and 4, the bottom of volume limiting chamber 20 is closed by lower end cap 54 which defines outlet conduit 56 for fluidly connecting the volume limiting chamber to drip chamber 22. Drip chamber 22 (not shown) is adhesively secured to annular flange 58 of lower end cap 54. Cylindrical portion 60 of lower end cap 54 defines drop forming orifice 62 at its lower end for forming parenteral solution into drops of predetermined size. The upper surface of lower end cap 54 has a plurality of concentric grooves 64 (e.g., 0.04 inch wide and 0.02 inch deep) and adjacent concentric support rings 66 (e.g., 0.02 inch wide) formed therein. The upper surfce of lower end cap 54 also defines annular flat sealing surface 68 (e.g., 0.060 inch wide) around its outer periphery against which membrane valve 70 (e.g., 0.95 inch diameter × 0.005 inch thick disk) is adapted to seal while being supported by concentric support rings 66. Concentric grooves 64 are interconnected by radial grooves 72 which divide the concentric support rings into semi-circular segments. As seen in FIG. 4, radial grooves 72 in adjacent concentric support rings are radially spaced apart 90° from one another. Parenteral solution which passes through membrane valve 70 can pass through concentric grooves 64 and radial grooves 72 as shown by the arrows in FIG. 4. For example, parenteral solution entering the outermost one of concentric grooves 64 can wind its way through the maze of concentric and radial grooves until it enters outlet conduit 56. Radial grooves 72 in adjacent concentric support rings are radially spaced apart from one another in order to avoid deformation of membrane valve 70.

Also attached to the outlet end of lower portion 40 of the volume limiting chamber is bypass member 74. Bypass member 74 has annular flange 76 which extends into an annular opening defined between lower portion 40 of the volume limiting chamber and lower end cap 54. The lower surface 80 of bypass member 74 is spaced from the upper surface of membrane valve 70 and defines chamber 82 (e.g., 0.010 inch thick) therebetween. Boss 84 of bypass member 74 defines discharge conduit 85 which has its longitudinal axis aligned with the longitudinal axis of outlet conduit 56. Attached to boss 84 are reinforcing ribs 86 which extend radially outwardly from boss 84. Bypass member 74 also defines slots 88 which are formed in the upper surface 90 of bypass member 74. Slots 88 extend radially outwardly from boss 84 along the same radial axes as radial grooves 72. Slots 88 are radially spaced apart 45° from reinforcing ribs 86. Bypass member 74 has grooves 92 formed in its lower surface 80 which extend radially outwardly from the center of the bypass member. The radial axes of grooves 92 correspond with the radial axes of slots 88 but grooves 92 extend further radially outwardly to annular flange 76. Bypass member 74 also includes annular groove 94 extending around the outer periphery of its lower surface 80. Annular groove 94 connects with radially extending grooves 92. In order to allow air bypass around the outer periphery of the membrane valve, valve 70 is spaced (e.g., 0.010 inch) from annular flange 76 at 96.

Membrane valve 70 preferably comprises a membrane filter. In general, any membrane filter can be used which will pass parenteral solution when wet at substantially zero pressure drop but will not pass air under normal pressures involved in intravenous administration. These filter materials, which are well know in the art, generally have a mean pore size of about 0.8 to 5 microns. Naturally, the particular filter material employed should be physiologically inert as well as chemically inert to the parenteral solution. The presently preferred membrane filter is sold by Millipore Corp., Bedford, Massachusetts, as filter type SM. This membrane filter comprises mixed esters of cellulose and has a mean pore size of 5.0 microns and a bubble point of 6 psi. The bubble point is the pressure required to force air through the pores of a water-wet filter. This membrane filter is more dense when wet with parenteral solution than typical parenteral solutions such as Ringers, Lactated Ringers, 5 percent Dextrose and Normal Saline and accordingly is more easily sealed against flat sealing surface 68.

The volume limited administration of parenteral solution using the intravenous set shown in FIG. 1 will now be described. Upper and lower compression clamps 16 and 24, respectively, are closed and piercer 12 is inserted into the outlet of a parenteral solution container which is then appropriately suspended. Air cap 52 is then removed from air vent 50 and upper compression clamp 16 is opened to allow parenteral solution to enter volume limiting chamber 20. When the desired level of parenteral solution is reached by visual reference to indicia 42, 44, upper compression clamp 16 is closed. Medication may now be added to the parenteral solution in volume limiting chamber 20 through injection site 53. The intravenous set is now primed by squeezing and releasing drip chamber 22 until the drip chamber is about half filled.

A sterile needle is then attached to needle adapter 34. Lower compression clamp 24 is opened to allow parenteral fluid to displace air in the remainder of the system and then this clamp is closed. Venipuncture is then performed and the flow rate is slowly set by adjusting lower compression clamp 24 until the desired flow is read by reference to drip chamber 22. When the pre-measured volume of parenteral solution has been delivered, the flow of parenteral solution is automatically shut off by membrane valve 70. Medication may also be added by injecting through the shoulder of injection bulb 30 and/or through the rubber stopple on Y-injection site 28. Lower compression clamp 24 is closed to prevent medication from going up flexible tubing 26 during these injection operations. To refill volume limiting chamber 20, upper compression clamp 16 is slowly opened until the desired level in the volume limiting chamber is reached. The set can also be converted from volume limited to continuous parenteral solution administration as will be readily apparent.

Referring once again to the priming operation, squeezing of drip chamber 22 causes air to be displaced from the drip chamber into volume limiting chamber 20. First, air from drip chamber 22 is forced up outlet conduit 56 in lower end cap 54 and then passes through concentric grooves 64 and radial grooves 72 in the opposite direction to the arrows shown in FIG. 4. This flow of air acts as an air cushion and lifts membrane valve 70 off the upper surface of lower end cap 54. Accordingly, the air can bypass membrane valve 70 by flowing around the outer periphery of membrane valve 70 which is pressed against the lower surface 80 of bypass member 74 by the air cushion. More specifically, the air flows between membrane valve 70 and flat sealing surface 68, through annular space 96, into annular groove 94, along radially extending grooves 92 and through radially extending slots 88 into the interior of volume limitng chamber 20. When drip chamber 22 is released, membrane valve 70 is forced back onto the upper surfce of lower end cap 54. Membrane valve 70 seals against flat sealing surface 68 and is simultaneously supported by concentric support rings 66 as shown in FIG. 3. Thereafter, parenteral solution flows from the interior of volume limiting chamber 20 through discharge conduits 85 and 88 into chamber 82 and then through membrane valve 70 either directly into outlet conduit 56 or into concentric grooves 64. The parenteral solution in concentric grooves 64 flows along the path shown by the arrows in FIG. 4 and exits volume limiting chamber 20 through outlet conduit 56.

FIG. 5 shows another embodiment of the air bypass of the present invention. In this embodiment, membrane valve 70 is mounted in cylindrical rim 100 which is in turn mounted in the bottom of volume limiting chamber 20. Lower end cap 54, in addition to defining outlet conduit 56, also defines air passage conduit 102. Mounting member 104 is mounted on lower end cap 54 and defines air inlet 106 which is axially aligned with air passage conduit 102. Membrane valve 70 is sealed to mounting member 104 so that neither liquid nor air can pass between mounting member 104 and membrane valve 70. Mounting member 104 has upstanding flange 108 on which is securely mounted a segment of elastomeric tubing 110 which is closed at its upper end by end cap 112. A slit 114 is provided in elastomeric tubing 110. Elastomeric tubing 110 and slit 114 together act as a check valve to allow air to pass from drip chamber 22 into volume limiting chamber 20 but prevent parenteral solution from passing from the volume limiting chamber into the drip chamber. The geometry and wall thickness of the segment of elastomeric tubing 110 are functions of the parenteral solution administration pressures. However, a preferred size comprises a segment of tubing having a 0.132 inch inner diameter and a 0.183 inch outer diameter with a knife blade-thin slit formed therein. Suitable elastomeric tubings can be formed from silicone rubber as well as gum rubber and natural latex. With this arrangement, air is allowed to bypass wet membrane valve 70 when drip chamber 22 is squeezed during priming and thereby provide an intravenous set which is simply and easily primed without opening and closing the flow control clamps.

While two specific embodiments of the present invention have been illustrated, it should be understood that there are other embodiments falling within its scope. For example, the geometry and arrangement of the concentric grooves and support rings of the embodiment shown in FIGS. 3 and 4 can be changed without departing from the present invention. Accordingly, the present invention should not be limited to the specific embodiments illustrated, but only as defined in the appended claims.

I claim:

1. A volume limiting chamber for use in an intravenous set comprising a chamber having a top and a bottom and side walls connecting said top and bottom, an inlet passageway in said top for placing said chamber in fluid communication with a source of parenteral solution, an outlet passageway in said bottom for placing said chamber in fluid communication with an intravenous needle, indicia on said chamber for indicating the amount of parenteral solution in said chamber, a membrane valve positioned in said chamber and cooperating with said outlet fluid passageway so that all parenteral solution in said chamber flows through said membrane valve, said membrane valve comprising a material which when wet will pass parenteral fluid but will not pass air at normal intravenous administration pressures, and means for bypassing said membrane valve, said means allowing air to enter said chamber through said bottom from underneath said membrane valve when said membrane valve is wet.

2. The volume limiting chamber of claim 1 in which said bypass means comprises means for mounting said membrane valve in said bottom so that air can enter said volume limiting chamber around the periphery of said membrane valve.

3. The volume limiting chamber of claim 2 in which said mounting means comprises a surface against which said membrane valve is adapted to seat, said surface having a plurality of air passages formed therein in communication with said outlet passageway such that air forced through said outlet passageway and said air passages will act to unseat said membrane valve.

4. The volume limiting chamber of claim 3 in which said mounting means further comprises a bypass member spaced from said surface to define a membrane valve chamber therebetween, said membrane valve being mounted in said membrane valve chamber.

5. The volume limiting chamber of claim 4 in which said bypass member has air passages communicating with said membrane valve chamber and the interior of said volume limiting chamber.

6. The volume limiting chamber of claim 5 in which said air passages in said bypass member comprise an annular groove positioned adjacent the outer peripheral surface of said membrane valve and a plurality of radially extending passages connecting with said annular groove.

7. The volume limiting chamber of claim 6 in which said bypass member has upper and lower surfaces and said plurality of radially extending passages comprise a plurality of radially extending grooves in said lower surface of said bypass member communicating directly with said annular groove and a plurality of radially extending slots in said upper surface of said bypass member communicating directly with said radially extending grooves.

8. The volume limiting chamber of claim 3 in which said plurality of air passages comprise concentric grooves formed in said surface of said mounting means.

9. The volume limiting chamber of claim 1 in which said bypass means comprises an air passageway in said bottom and check valve means associated with said air passageway for allowing air to enter said chamber through said air passageway and preventing parenteral solution from exiting said chamber through said air passageway.

10. The volume limiting chamber of claim 9 in which said check valve means comprises a segment of elastomeric tubing.

11. The volume limiting chamber of claim 10 in which said segment of elastomeric tubing comprises a segment of silicone rubber tubing having a slit formed therein.

12. An intravenous set comprising a volume limiting chamber for controlling the volume of parenteral solution administered to a patient and a flexible drip chamber for determining the parenteral solution flow rate positioned downstream of said volume limiting chamber, said volume limiting chamber including a top and bottom and side walls connecting said top and bottom, an inlet passageway in said top for placing said volume limiting chamber in fluid communication with a source of parenteral solution, an outlet passageway in said bottom for placing said volume limiting chamber in fluid communication with said drip chamber, indicia on said volume limiting chamber for indicating the amount of parenteral solution in said volume limiting chamber, a membrane valve positioned in said bottom of said volume limiting chamber and cooperating with said outlet passageway so that all parenteral solution in said volume limiting chamber flows through said membrane valve, said membrane valve comprising a material which when wet will pass parenteral solution but will not pass air at normal intravenous administration pressures, and means for bypassing said membrane valve and allowing air to enter said volume limiting chamber from said drip chamber when said membrane valve is wet and said drip chamber is squeezed.

13. The intravenous set of claim 12 in which said bypass means comprises means for mounting said membrane valve in said bottom so that air can enter said volume limiting chamber around the periphery of said membrane valve.

14. The intravenous set of claim 13 in which said mounting means comprises a surface against which said membrane valve is adapted to seat, said surface having a plurality of air passages formed therein in communication with said outlet passageway such that air forced through said outlet passageway and said air passages will act to unseat said membrane valve.

15. The intravenous set of claim 14 in which said mounting means further comprises a bypass member spaced from said surface to define a membrane valve chamber therebetween, said membrane valve being mounted in said membrane valve chamber.

16. The intravenous set of claim 15 in which said bypass member has air passages communicating with said membrane valve chamber and the interior of said volume limiting chamber.

17. The intravenous set of claim 16 in which said air passages in said bypass member comprise an annular groove positioned adjacent the outer peripheral surface of said membrane valve and a plurality of radially extending passages connecting with said annular groove.

18. The intravenous set of claim 17 in which said bypass member has upper and lower surfaces and said plurality of radially extending passages comprise a plurality of radially extending grooves in said lower surface of said bypass member communicating directly with said annular groove and a plurality of radially extending slots in said upper surface of said bypass member communicating directly with said radially extending grooves.

19. The intravenous set of claim 14 in which said plurality of air passages comprise concentric grooves formed in said surface of said mounting means.

20. The intravenous set of claim 12 in which said bypass means comprises an air passageway in said bottom and check valve means associated with said air passageway for allowing air to enter said chamber through said air passageway and preventing parenteral solution from exiting said chamber through said air passageway.

21. The intravenous set of claim 20 in which said check valve means comprises a segment of elastomeric tubing.

22. The intravenous set of claim 21 in which said segment of elastomeric tubing comprises a segment of silicone rubber tubing having a slit formed therein.

23. A valve for use in an intravenous set comprising a membrane which when wet will pass parenteral fluid but will not pass air at normal intravenous administration pressures and means for mounting said membrane so that air can bypass said membrane when wet, said mounting means comprising a surface against which said membrane is adapted to seat with an airtight seal, said surface having air passage means formed therein such that air forced through said air passage means will unseat said membrane, said mounting means further comprising means for restraining the movement of said membrane when unseated.

24. The valve of claim 23 in which said restraining means comprises a bypass member spaced from said surface to define a membrane chamber therebetween, said membrane being mounted in said membrane chamber.

25. The valve of claim 24 in which said bypass member has air passages communicating with said membrane chamber.

26. The valve of claim 25 in which said air passages in said bypass member comprise an annular groove positioned adjacent the outer peripheral surface of said membrane and a plurality of radially extending passages connecting with said annular groove.

27. The valve of claim 26 in which said bypass member has upper and lower surfaces and said plurality of radially extending passages comprise a plurality of radially extending grooves in said lower surface of said bypass member communicating directly with said annular groove and a plurality of radially extending slots in said upper surface of said bypass member communicating directly with said radially extending grooves.

28. The valve of claim 23 in which said air passage means comprise a plurality of concentric grooves formed in said surface of said mounting means against which said membrane is adapted to seat.

29. A filter for use in an intravenous set comprising a membrane which will filter parenteral fluid and means for housing said membrane including a surface against which said membrane when wet is adapted to seat with an airtight seal at normal intravenous administration pressures, said housing means further comprising means for restraining the movement of said membrane when unseated so that said membrane is confined adjacent to said surface, said membrane being unattached to said housing means.

30. The filter of claim 29 in which said restraining means comprise a member spaced from said surface to define a membrane chamber therebetween, said membrane being confined in said membrane chamber.

31. The filter of claim 29 in which said membrane when wet will pass parenteral fluid but will not pass air at normal intravenous administration pressures.

32. The filter of claim 31 in which said membrane has a mean pore size of about 0.8 to 5 microns.

33. The filter of claim 31 in which said membrane when wet is more dense than said parenteral fluid.

34. The filter of claim 29 in which said membrane comprises mixed esters of cellulose.

35. The valve of claim 23 in which said membrane comprises mixed esters of cellulose.

36. An intravenous set comprising a volume limiting chamber for controlling the volume of parenteral solution administered to a patient and a flexible drip chamber for determining the parenteral solution flow rate positioned downstream of said volume limiting chamber, said volume limiting chamber including a top and bottom and side walls connecting said top and bottom, an inlet passageway in said top for placing said volume limiting chamber in fluid communication with a source of parenteral solution, an outlet passageway in said bottom for placing said volume limiting chamber in fluid communication with said drip chamber, indicia on said volume limiting chamber for indicating the amount of parenteral solution in said volume limiting chamber, a membrane valve positioned adjacent to said outlet passageway and cooperating with said outlet passageway so that all parenteral solution in said volume limiting chamber flows through said membrane valve, said membrane valve comprising a material which when wet will pass parenteral solution but will not pass air at normal intravenous administration pressures, and means for bypassing said membrane valve and allowing air to enter said volume limiting chamber from said drip chamber when said membrane valve is wet and said drip chamber is squeezed.

* * * * *